(12) United States Patent
Zayas (10) Patent No.: US 7,795,813 B2
(45) Date of Patent: Sep. 14, 2010

(54) ULTRAVIOLET LAMP FOR USE IN WATER PURIFIERS

(75) Inventor: Betty Jean Zayas, Bridgeport, CT (US)

(73) Assignee: Light Sources, Inc., Orange, CT (US)

( * ) Notice: Subject to any disclaimer, the term of this patent is extended or adjusted under 35 U.S.C. 154(b) by 379 days.

(21) Appl. No.: 11/870,256

(22) Filed: Oct. 10, 2007

(65) Prior Publication Data

US 2008/0246402 A1  Oct. 9, 2008

Related U.S. Application Data

(63) Continuation-in-part of application No. 11/675,315, filed on Feb. 15, 2007, now Pat. No. 7,390,222.

(60) Provisional application No. 60/777,213, filed on Feb. 27, 2006.

(51) Int. Cl.
*H01J 17/02* (2006.01)
(52) U.S. Cl. .................................................... 313/624
(58) Field of Classification Search ................. 313/624, 313/25–27, 318.01, 318.02
See application file for complete search history.

(56) References Cited

U.S. PATENT DOCUMENTS

| | | | |
|---|---|---|---|
| 2,135,267 A | 11/1938 | Alden | |
| 2,297,188 A | 9/1942 | Joyce | |
| 3,059,214 A | 1/1960 | Heller | |
| 3,761,862 A | 9/1973 | Spiteri | |
| 4,075,531 A | 2/1978 | Marino | |
| 4,256,989 A | 3/1981 | Trutner et al. | |
| 4,528,429 A | 7/1985 | Dobson et al. | |
| 4,740,169 A | 4/1988 | Gordon | |
| D300,215 S | 3/1989 | Brenner et al. | |
| 4,990,099 A | 2/1991 | Marin et al. | |
| 5,040,993 A | 8/1991 | Krug et al. | |
| 5,120,268 A | 6/1992 | Gerrans | |
| 5,166,527 A | 11/1992 | Solymar | |

(Continued)

FOREIGN PATENT DOCUMENTS

GB  694114  7/1953

(Continued)

OTHER PUBLICATIONS

Kaifeng, H., et al. "Design of a Fluorescent Lamp Control Platform Based on Power-line Carrier," Electronic Measurement and Instruments, 2007. ICEMI 2007, 8th International Conference, Aug. 16, 2007-Jul. 18, 2007: p. 1.

(Continued)

*Primary Examiner*—Toan Ton
*Assistant Examiner*—Hana S Featherly
(74) *Attorney, Agent, or Firm*—Cantor Colburn, LLP (57) ABSTRACT

A lamp is provided having terminal pins mounted on and extending outwardly along a longitudinal axis of an end cap of the lamp. The pins are offset relative to one another along the longitudinal axis. The end cap has semi-circular, parallel surfaces with an asymmetrical section or recess at one end, and the pins extend outwardly from the respective semi-circular, parallel surfaces. A barrier wall extends substantially perpendicularly between the semi-circular surfaces.

4 Claims, 8 Drawing Sheets

U.S. PATENT DOCUMENTS

| | | |
|---|---|---|
| 5,422,487 A | 6/1995 | Sauska et al. |
| 5,471,063 A | 11/1995 | Hayes et al. |
| 5,634,820 A | 6/1997 | Vakil |
| 5,727,963 A | 3/1998 | Lemaster |
| 6,165,013 A | 12/2000 | Broussard |
| 6,250,947 B1 | 6/2001 | Holzer |
| 6,634,902 B1 | 10/2003 | Pirovic |
| 6,641,419 B1 | 11/2003 | Richardson |
| 6,884,103 B1 | 4/2005 | Kovacs |
| 7,137,728 B2 | 11/2006 | Witham et al. |
| 7,354,284 B2 | 4/2008 | Aime et al. |
| 7,390,222 B2 | 6/2008 | Ciancanelli et al. |
| 7,390,225 B2 | 6/2008 | Elku et al. |
| D575,742 S | 8/2008 | Scherer |
| 2004/0247251 A1 | 12/2004 | Rubino et al. |
| 2008/0197291 A1 | 8/2008 | Gerardi-Fraser et al. |

FOREIGN PATENT DOCUMENTS

| | | |
|---|---|---|
| WO | 2006/136026 | 12/2006 |

OTHER PUBLICATIONS

International Search Report with Written Opinion, PCT/US08/54118, Date Mailed Oct. 24, 2008.

International Search Report with Written Opinion, PCT/US08/54121, Date Mailed Nov. 3, 2008.

International Search Report with Written Opinion, PCT/US07/04396, Date Mailed Aug. 20, 2008.

ULTRAVIOLET LAMP FOR USE IN WATER PURIFIERS

CROSS REFERENCE TO RELATED APPLICATIONS

This application is a continuation in part (CIP) of application Ser. No. 11/675,315 filed Feb. 15, 2007 which claimed the benefit of the date of earlier filed provisional application, U.S. Provisional Application No. 60/777,213, filed on Feb. 27, 2006, the contents of both of which are incorporated by reference herein, and priority to both which is claimed herein.

BACKGROUND OF THE INVENTION

1. Field of the Invention

This invention generally relates to improvements in lamps, especially ultraviolet lamps used in air and water purifiers.

2. Description of Related Art

Ultraviolet air and water or other liquid purifiers are known for disinfecting contaminated air or water or other liquid for domestic or commercial use. Such purifiers include at least one lamp for emitting ultraviolet radiation into a chamber filled with contaminated air or water or other liquid to kill microorganisms therein. In conventional manner, the lamp includes two electrodes spaced apart within an elongated arc tube containing a gas, particularly mercury vapor with or without additives. A pair of end caps are mounted at the ends of the tube. Each electrode contains two lead wires from the lamp seal each of which, or in some instances only one, are electrically connected to respective contact(s) or terminal pin(s). The lamp is typically inserted endwise into a sleeve installed in the water, other liquid or air purifier with or without the sleeve. To simplify insertion and electrical connection, the pins are conveniently mounted on one of the end caps. When the electrodes are energized by voltage from an electrical power supply, an electrical discharge is initiated in the gas between the electrodes. This discharge reacts with a layer of a radiation-emitting material coated on an interior surface of the arc tube and causes ultraviolet radiation to be emitted from the lamp in a manner well known in the art.

An example of an ultraviolet lamp of the type described above is disclosed in U.S. Pat. No. 5,166,527 ('527), all of the contents of which are incorporated herein by reference. The '527 patent discloses a lamp, especially useful as an ultraviolet lamp for use in a water purifier, comprising an elongated, hollow arc tube extending along a longitudinal axis between opposite end regions. The tube contains a gas, preferably mercury vapor with or without additives. A pair of electrodes is spaced apart along the longitudinal axis. The electrodes are respectively mounted within the arc tube at the end regions thereof. A pair of end caps is respectively mounted at the end regions of the arc tube. A first electrical contact or pair of electrical contacts or terminal pins extends in mutual parallelism along the longitudinal axis and is electrically connected to one or both of the electrode lead wires. A second electrical contact or pair of electrical contacts or terminal pins extends in mutual parallelism along the longitudinal axis and is electrically connected to one or both of the other of the electrode lead wires. Both pairs of pins are mounted on, and extend outwardly along the longitudinal axis of, one of the end caps. A wire conductor is, or two wire conductors are, located exteriorly of the tube and electrically connected to one pin or one pair of pins at one end region of the tube, as well as to the electrode at the other end region of the tube.

Figure 1:
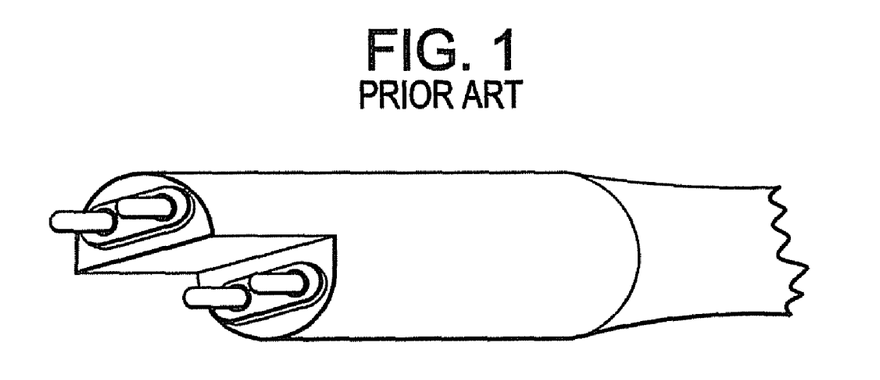
FIGS. 1-7 are respective views of end caps used in ultraviolet lamps in accordance with the prior art.
Figure 2:
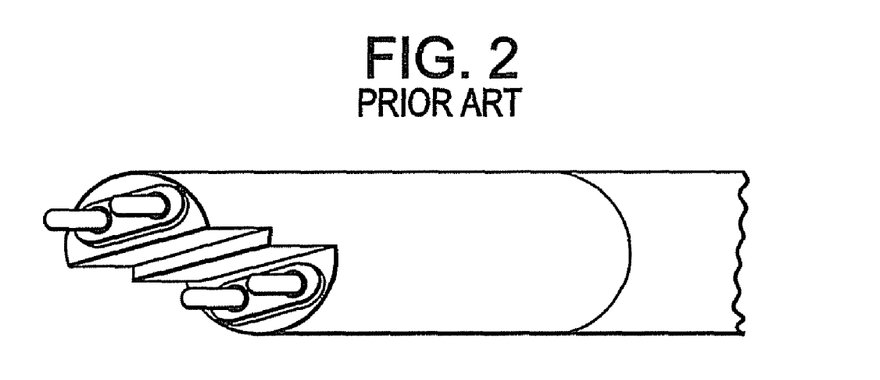
Figure 3:
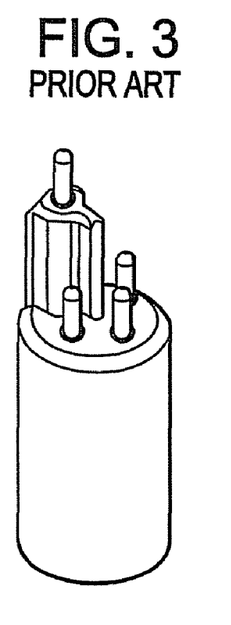
Figure 4:
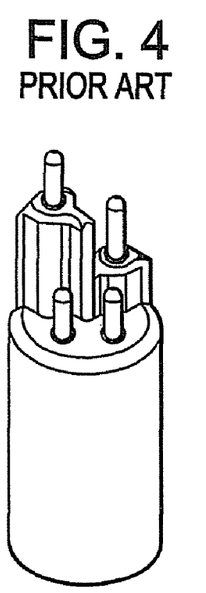
Figure 5:
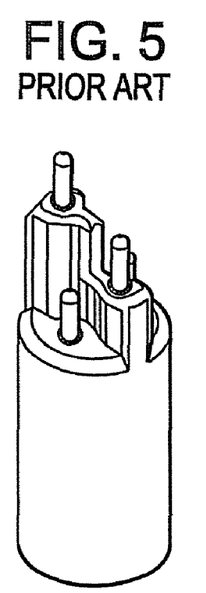
Figure 6:
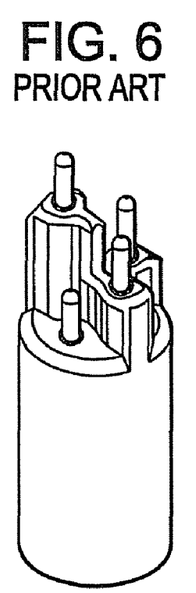
Figure 7:
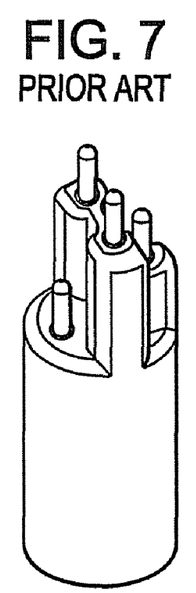

Two embodiments, of the lamp disclosed in the '527 patent are shown in prior art FIGS. 1 and 2. As shown in FIGS. 1 and 2, the pairs of pins are offset relative to each other along the longitudinal axis. This offset resists the formation of an electrical arc between the pairs of pins exteriorly of the arc tube, especially in the presence of the moisture-laden, humid environment of the water purifier.

Still referring to prior art FIGS. 1 and 2, the one end cap has a stepped outer end wall having a pair of wall portions lying in mutual parallelism in planes generally perpendicular to the longitudinal axis. The first pair of pins is supported on, and extends through, one of the end wall portions for a predetermined distance, and the second pair of pins is supported on, and extends through, the other of the end wall portions for the same predetermined distance. The planes of the end wall portions are spaced apart by a predetermined spacing larger than said predetermined distance in order to still further prevent electrical arcing between the pairs of pins exteriorly of the arc tube. A barrier wall internally of the one end cap physically separates the electrical connections to the two pairs of pins to resist the formation of an electrical arc between the pairs of pins interiorly of the one end cap. The barrier wall is advantageously made of the same non-conductive material as the one end cap.

In addition to the two-tiered stepped bases of the '527 patent, other multi-tiered bases have been manufactured including those bases shown in prior art FIGS. 3-7.

Although well-suited for their intended purposes, there continues to be a need for improved lamp base designs, particularly ultraviolet lamps.

There are many different types of lamps that have a base or end cap that can be connected with a socket to provide electrical connections to the lamps. The end cap and socket must be constructed to permit easy replacement of the lamp while securely holding the lamp. This may be particularly important in certain applications where vibration or movement of the lamp or lamp fixture could result in unintentional separation between the lamp's end cap and the socket. Additionally, the electrical connections must remain secure.

In some applications where a multiplicity of contact pins and/or pin orientations is utilized, it is often difficult to align the contact pins to make the electrical connection necessary to operate the lamp. Often, the contact pins may become misaligned or bent due to their extension or projection from the base of the lamp, preventing their insertion into a socket. It may also be possible to insert the end cap into a socket such that the contacts are not connected with the proper terminals in the socket, resulting in improper operation of the lamp. Also, on a typical "slide into place" male/female pin connector there is no locking or twist locking and thus the pins may slide out and become disconnected easily by vibration for example.

An example of an ultraviolet lamp of the type described above is disclosed in U.S. Pat. No. 5,166,527 ('527), which uses a stepped base with pins connector, all of the contents of which are incorporated herein by reference. The '527 patent discloses a lamp or bulb, used as an ultraviolet lamp for use in an air or water purifier, comprising an elongated, hollow arc tube extending along a longitudinal axis between opposite end regions. The tube contains a gas, preferably mercury vapor with or without additives. A pair of electrodes is spaced apart along the longitudinal axis. The electrodes are respectively mounted within the arc tube at the end regions thereof. A pair of end caps is respectively mounted at the end regions of the arc tube. A first electrical contact or pair of electrical contacts or terminal pins extends in mutual parallelism along the longitudinal axis and is electrically connected to one or both of the electrode lead wires. A second electrical contact or pair of electrical contacts or terminal pins extends in mutual parallelism along the longitudinal axis and is electrically connected to one or both of the other of the electrode lead wires. Both pairs of pins are mounted on, and extend outwardly along the longitudinal axis of, one of the end caps. A wire conductor is, or two wire conductors are, located exteriorly of the tube and electrically connected to one pin or one pair of pins at one end region of the tube, as well as to the electrode at the other end region of the tube. This design is mainly designed to prevent electrical arcing and does not lock in place.

As noted in WO/2006/136026 to Elku et al. which is a variation of the slide-on pin connector above, a potential problem with this approach is that in many applications, the radiation lamp is immersed in a flow of water and turbulence created within that water treatment system invariably imparts a vibratory motion to the lamps which frequently results in lamps being vibrated or shaken loose of its electrical connection base or socket thereby causing the lamps to be rendered completely or intermittently inoperative. When such an event occurs, the water being treated may not be fully disinfected. The prior art has attempted to address this problem by using a relatively complicated mechanical connection (e.g., a so-called "push-and-twist" connection) to secure the lamp to the connection base. See, for example, U.S. Pat. No. 5,422,487 to Sauska et al. and U.S. Pat. No. 6,884,103 to Kovacs. The potential problem with these approaches is the complexity of the mechanical connection between the lamp and the base unit requiring the use of springs, specialized connection lugs and the like. Further, a connection system which is predicated on a dual motion system such that pushing and twisting if used incorrectly for example may give rise to higher incidents of lamp breakage, electrical shock, and other damage to the lamp by field personal. Therefore, eliminating a forceful "push" necessary to deflect a heavy locking spring in a "push and twist" lock would be beneficial because the typically glass lamp would be subject to reduced force and stress.

Also, it is important for safety that lamps of proper wattage be used for safety, heat, and fire concerns, thus a unique keying system which only allows lamps of proper wattage to be inserted into the base will also help safety.

Accordingly, there remains the need in the art for a safety lamp device, particularly a radiation lamp, which will provide a reliable, locking, and secure from movement electric connection, yet be relatively inexpensive, uncomplicated, durable, rugged, and simple to implement with smooth operation and with reduced force and stress on the lamp for safety purposes. Also, a lamp that reduces the chance of electrical shock is needed for safety purposes.

Thus, there continues to be a need for improved lamp base designs, particularly ultraviolet lamps.

SUMMARY OF THE INVENTION

In accordance with the present invention, a lamp is provided having terminal pins mounted on and extending outwardly along a longitudinal axis of an end cap of the lamp. The pins are offset relative to one another along the longitudinal axis. The end cap has semi-circular, parallel surfaces at one end, and the pins extend outwardly from the respective semi-circular, parallel surfaces. A barrier wall extends substantially perpendicularly between the semi-circular surfaces. In a first embodiment, a male extension member extends outwardly from the barrier wall along at least a portion of the lower semi-circular surface. This male extension is coextensive with the upper semi-circular surface. Alternatively, in a second embodiment, a female recess is provided through the boundary wall. This recess again extends between the upper and lower semi-circular surfaces.

The above-described end cap configuration for the lamp of this invention may be mated to a complimentary shaped receptacle. It will be appreciated that if the male member embodiment is used in the end cap of the lamp, a complimentary shaped receptacle will be the inverse (that is, a female configuration). Similarly, if the female type end cap is utilized as the lamp end cap, the complimentary receptacle will have a male extension.

The utilization of the male or female configuration along the boundary wall in accordance with the present invention leads to improved lamp configurations in that polarization between the pairs of pins are more easily ensured; and the mating of the end cap and receptacle may be stronger. The designs will further allow for matching of the lamp and connector to a specific power supply to reduce the chances of connecting an ultraviolet lamp into an improperly matched power supply.

The lamp of this invention is preferably an ultraviolet lamp and finds particular application for use in a water, other liquid, or air purifier.

BRIEF DESCRIPTION OF THE DRAWINGS

Referring now to the drawings wherein like elements are numbered alike in the several FIGURES.

DETAILED DESCRIPTION OF THE PREFERRED EMBODIMENT

Figure 8:
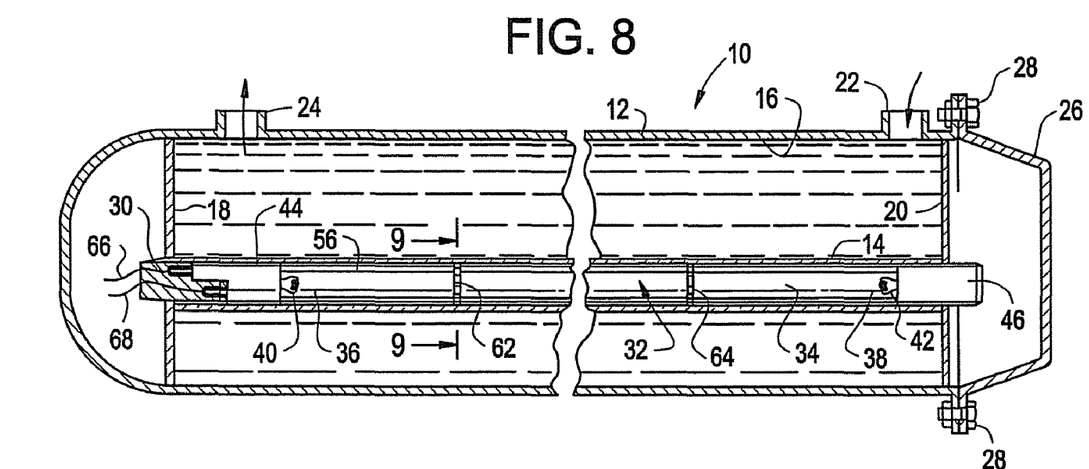
FIG. 8 is a cross-sectional view along the longitudinal axis of a water purifier employing the ultraviolet lamp in accordance with the present invention.
Figure 9:
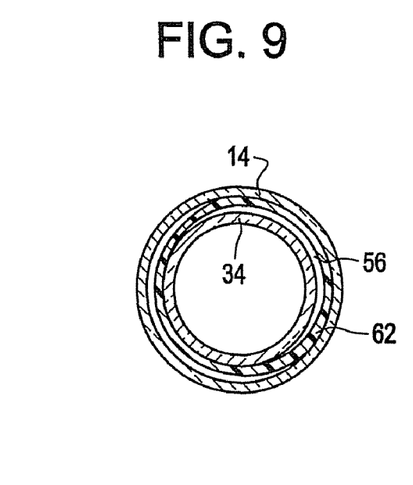
FIG. 9 is a cross-sectional elevation view along the line 9-9 of FIG. 8.

Referring now to FIG. 8 of the drawings, reference numeral 10 generally identifies a water purifier having a cylindrical housing 12 extending along a longitudinal axis. A hollow, axially-extending sleeve 14 is centrally mounted within the housing 12 between apertured support walls 18, 20 spaced apart along the longitudinal axis. The support walls 18, 20, together with the interior wall of the housing 12 and the exterior wall of the sleeve 14, bound an interior space 16. A water inlet 22 admits pressurized water to be purified into the space 16. A water outlet 24 discharges the purified water from the space 16. The space 16 serves as a flow-through passage for the water contained therein which, during the course of its flow, is exposed to ultraviolet radiation as described below.

A removable cover 26 overlies the support wall 18 at one end of the housing 12. The cover 26 is detachably coupled to the housing 12 by a set of threaded fasteners 28 to permit access to the interior of the sleeve 14 through the aperture of the support wall 18. An electrical socket 30 is removably mounted within the aperture of the support wall 18. An ultraviolet lamp 32 in accordance with this invention is slidably inserted into the interior of the sleeve 14 through the aperture of the support wall 18. An electrical connection, as described below, is made with the socket 30. In operation, the lamp 32 emits ultraviolet radiation of sufficient intensity to kill microorganisms in the water, other liquid or air contained in the space 16 to purify the same for domestic and commercial applications.

The lamp 32 includes an elongated, hollow, sealed, arc tube 34 constituted of a light-transmissive material, e.g. silica quartz or other ultraviolet transmitting glass tube. The tube 34 has opposite end regions 36,38 spaced apart along the longitudinal axis. A gas, preferably mercury vapor with or without additives, is sealingly contained within the tube.

A pair of electrodes 40, 42 is respectively mounted within the tube at the end regions 36, 38. A pair of end caps 44, 46 constituted of a non-conducting material, e.g. ceramic, is respectively mounted at the end regions 36, 38 over the sealed end regions of the tube. Each end cap has a bore having a closed base against which a sealed end region of the tube abuts when the sealed end region is inserted fully into a respective end cap. End cap 44 (best show in FIGS. 10 and 10A) also has a barrier wall 70a, 70b, extending between semi-circular bases 72, 74 such that bases 72, 74 are stepped with base 72 being the upper or distal base and base 74 being the lower or proximal base. In accordance with an important feature of this invention, a male member 75 extends laterally from barrier wall 70a, 70b, along lower base 74. Member 75 is centrally positioned along wall 70a, 70b thus splitting the wall into the two sections 70a and 70b. Member 75 has a height which is equal to the distance between respective bases 72 and 74. Member 75 also acts to divide lower base 74 into two symmetrical sections (each comprising an approximately 90 degree quadrant).

Figure 10:
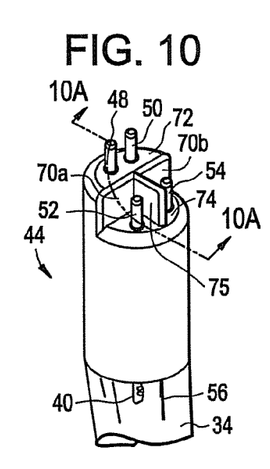
FIG. 10 is a perspective elevation view of a first embodiment of an end cap for a lamp in accordance with the present invention.
Figure 10A:
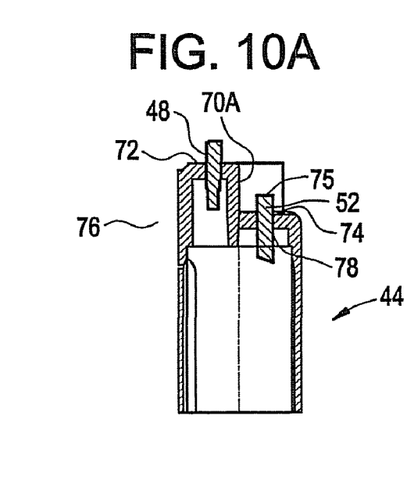
FIG. 10A is a cross-sectional elevation view along the line 10A-10A of FIG. 10.
Figure 11:
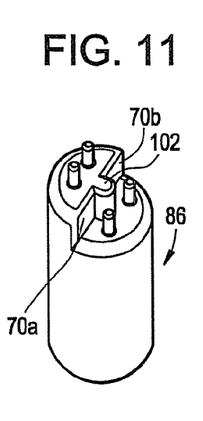
FIGS. 11-14 are perspective elevation views of second, third, fourth and fifth embodiments of end caps in accordance with the present invention.
Figure 12:
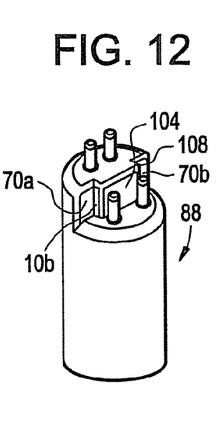

Still referring to FIG. 10, a first pair of electrical contacts or terminal pins 48, 50 extends in mutual parallelism along the longitudinal axis, and is mounted on, and extends outwardly of, the end cap 44 (through base 72). A second pair of electrical contacts or terminal pins 52, 54 also extends in mutual parallelism along the longitudinal axis, and is also mounted on, and extends outwardly of, the same end cap 44 (through base 74). Pins 52 and 54 are separated from one another by member 75. The pins 48, 50 extend into interior compartment 76, and the pins 52, 54 extend into compartment 78 (see FIG. 10A).

The pins 48, 50 are electrically connected within end cap 44 to one end of a wire conductor 56. The conductor 56 is located exteriorly of the tube 34, and extends along the longitudinal axis to the opposite end cap 46 wherein the other end of the conductor 56 is connected to the electrode 42. The pins 52, 54 are electrically connected within the end cap 44 to the electrode 40. The barrier wall 70a, 70b physically separates the pairs of pins.

Figure 15:
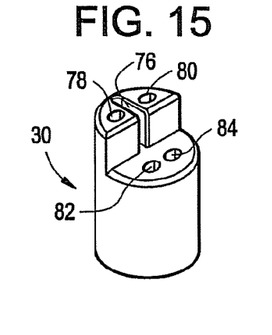
FIGS. 15-19 are perspective elevation views of receptacles for the end caps of FIGS. 10-14, respectively.
Figure 16:
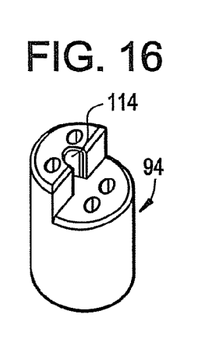
Figure 17:
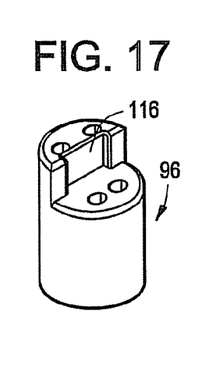
Figure 18:
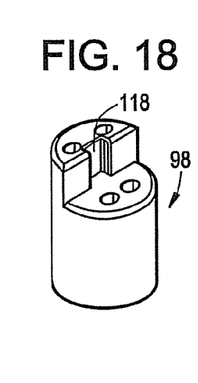
Figure 19:
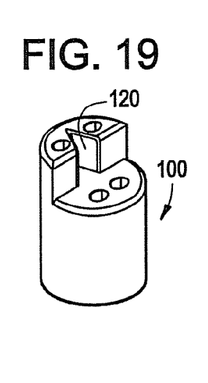
Figure 20:
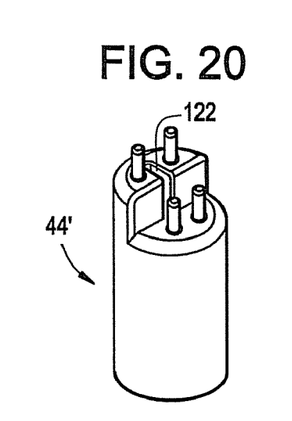
FIGS. 20-24 are perspective elevation views of additional embodiments of end caps having female recesses in accordance with yet other embodiments of the present invention.
Figure 21:
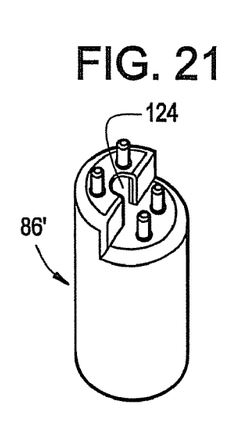
Figure 22:
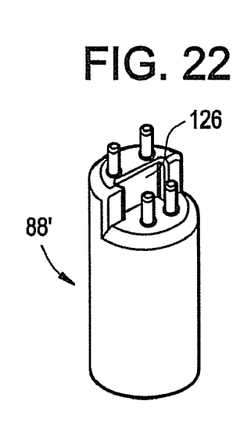

Thus, as shown in FIG. 10, the end cap 44 has a stepped, outer end wall having a pair of semi-circular end wall portions 72, 74 lying in mutual parallelism in planes generally perpendicular to the longitudinal axis. As best shown in FIG. 15, the socket 30 has a complementary stepped, outer end wall together with a centrally located recess 76. During mating, the pins 48, 50, 52, 54 will be received into respective sockets 78, 80, 82, 84 while member 75 is received into mating recess 76.

A set of centering rings 62, 64, preferably constituted of a synthetic plastic material, is located on tube 34, being placed thereon before the end caps are attached to the end regions of the tube 34. The rings 62, 64 coaxially surround the tube 34 and frictionally engage and support the tube, and assist in centering the tube within sleeve 14.

Figure 13:
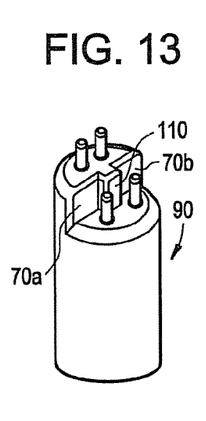
Figure 14:
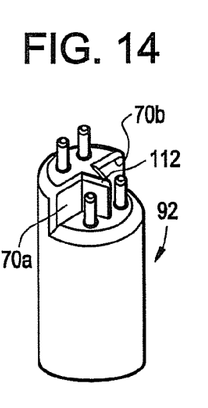

Referring now to FIGS. 11-14, additional embodiments of the end cap depicted in FIG. 10 are shown. All of these end caps have a similar configuration to that shown in FIG. 10 including a pair of parallel but longitudinally displaced semi-circular bases 72, 74 having a barrier wall 70a, 70b, extending therebetween so as to form a stepped base. In addition and in accordance with the present invention, a male member or extension extends centrally outwardly from barrier wall 70a, 70b. While this male extension was in the form of a relatively thin wall 75 in the end cap 44 of FIG. 10, the male extension takes on a differing geometric shape in the various embodiments shown in FIGS. 11-14. More specifically, the end cap 86 in FIG. 11 has a rounded arcuate shape (e.g., V-shaped, semi-circular shaped) extension 102 extending between barrier wall sections 70a and 70b. The end cap 88 in FIG. 12 has an extension 104 in the shape of a rectangular box which includes a pair of opposed sidewalls 106, 108 which extend outwardly from and perpendicularly to respective barrier wall sections 70a and 70b. The end cap 90 of FIG. 13 also has a box like extension 110 which is similar to extension 104 (in FIG. 12); however, extension 112 has a more square cross-section relative to the rectangular cross-section of extension 104. Thus, the barrier wall sections 70a and 70b in FIG. 13 are relatively larger than the respective barrier wall sections 70a and 70b in FIG. 12. End cap 92 in FIG. 14 is a V-shaped triangular shape extension member 112 which forms the divider between barrier wall sections 70a and 70b.

Significantly, all of the additional embodiments of FIGS. 11-14 have in common the feature of FIG. 10 wherein a male member extends outwardly from barrier wall 70a, 70b, and is coextensive with stepped (that is longitudinally displaced) base sections 72, 74. It will be appreciated that in accordance with this invention, the male member may have any suitable configuration besides those shown in FIGS. 10-14 and that such configuration may be symmetrical, asymmetrical, spherical, conical, aspheric or any other desired shapes.

As in the receptacle 30 shown in FIG. 15 which receives the end cap 44 in FIG. 10, the end caps of the embodiments of FIGS. 11-14 have similarly complimentary shaped respective receptacles 94, 96, 98 and 100 as shown in FIGS. 16-19, respectively. Thus, receptacle 94 of FIG. 16 has a rounded arcuate shaped recess 114 for receiving and mating with rounded or U-shaped extension 102 in FIG. 11. Similarly, receptacle 96 has a rectangular shaped recess 116 which is sized and configured to mate with and be received by rectangular extension 104 in FIG. 12. Receptacle 98 in FIG. 18 has a square shaped recess 118 for mating with and being received by square shaped extension 110 in FIG. 13 while receptacle 100 of FIG. 19 has a V-shaped recess 120 for mating with and being received by V-shaped extension 112 in FIG. 14. Again, it will be appreciated that the receptacles of FIGS. 15-19 may include a recess having any desired shape, so long as the shape is complimentary to, and can be received by, the shape of the extensions in the mating end cap.

Figure 23:
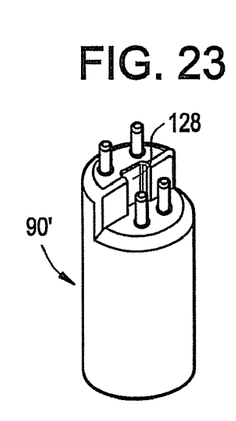
Figure 24:
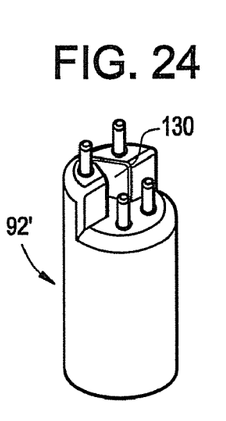

In still another alternative embodiment of the present invention, it will be appreciated that the male extension in the plug ended lamp and the female recess in the complimentary receptacle may be reversed such that the lamp cap will exhibit the recess while the receptacle will exhibit the complimentary male extension for mating with the recess in the cap. Such alternative configurations are shown in the end caps of FIGS. 20-24 and also in FIGS. 38-45. The end caps of FIGS. 20-24 and 38-45 are similar to the respective end caps shown in FIGS. 10-14 with the only difference being that the male extension has been substituted with the female recess in FIGS. 20-24. Thus, end cap 44' includes a narrow recess 122 (similar to the recess 76 shown in FIG. 15), end cap 86' and 86a include an arcuate shaped recess 124, 124a (similar to the recess 114 in FIG. 16), end cap 88' includes a rectangularly shaped recess 126 (similar to the recess 116 in FIG. 17), end cap 90' of FIG. 23 includes a square shaped recess 128 (similar to the recess 118 in FIG. 18) and end cap 92' of FIG. 24 includes a V-shaped recess 130 (similar to the V-shaped recess 120 of FIG. 19).

Figure 25:
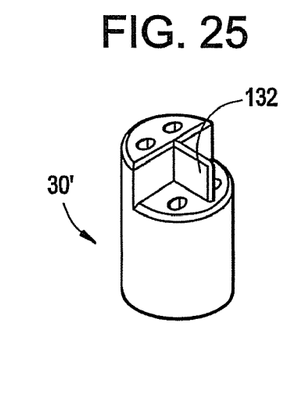
FIGS. 25-29 are perspective elevation views of receptacles for the end caps of FIGS. 20-24, respectively.
Figure 26:
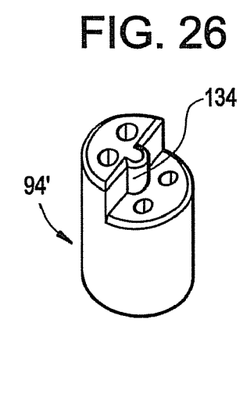
Figure 27:
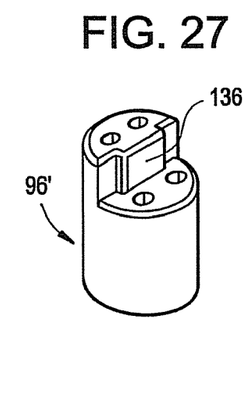
Figure 28:
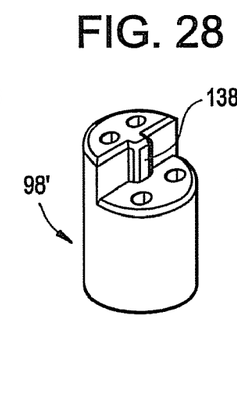
Figure 29:
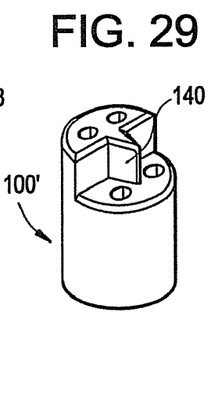
Figure 30:
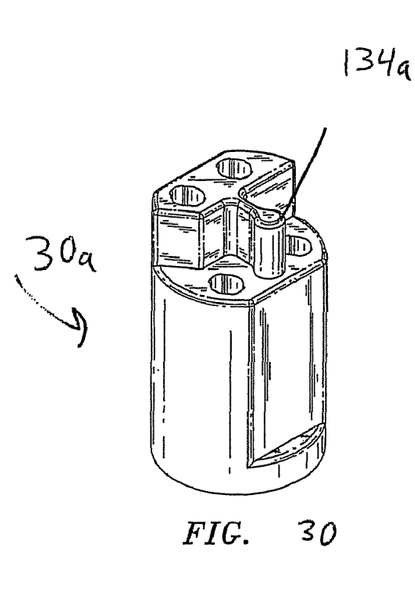
FIGS. 30-31 are perspective views of an embodiment of a socket useable with the lamp base shown in FIGS. 38-45.
Figure 31:
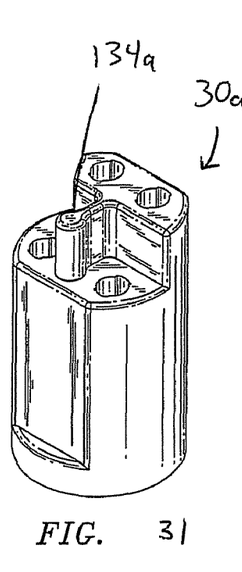
Figure 32:
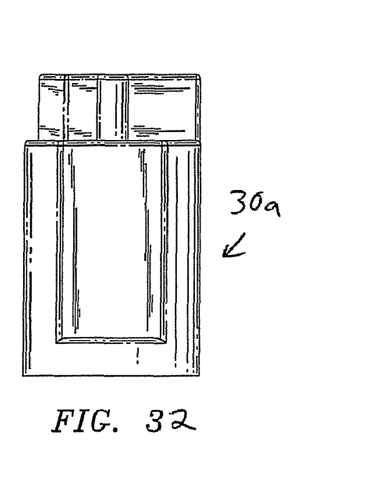
FIGS. 32-35 are side views of the embodiment shown in FIGS. 30-31.
Figure 33:
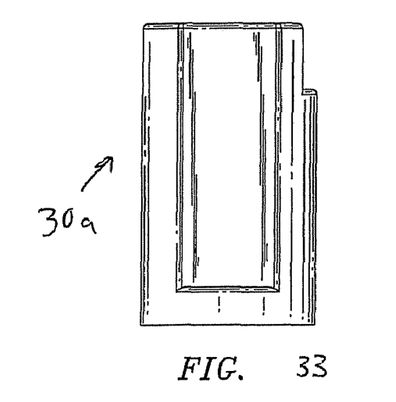
Figure 34:
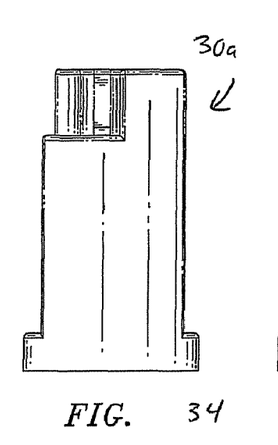
Figure 35:
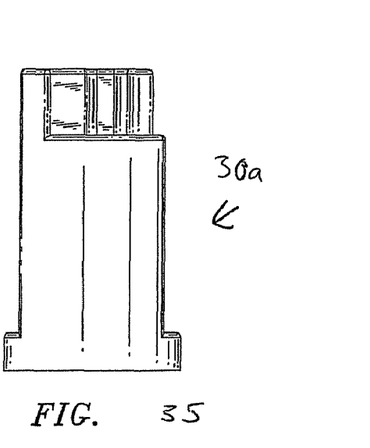
Figure 36:
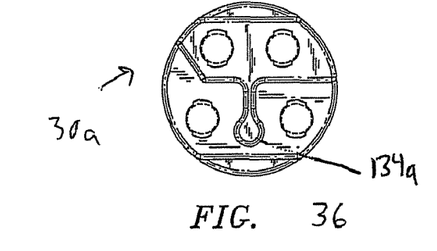
FIG. 36 is a top plan view of the embodiment shown in FIGS. 30-35
Figure 37:
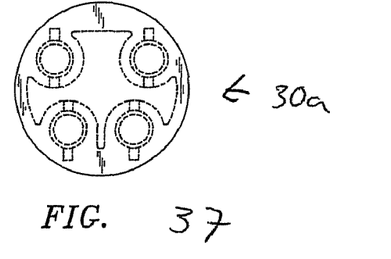
FIG. 37 is a bottom plan view of the embodiment shown in FIG. 30-35.
Figures 38, 39:
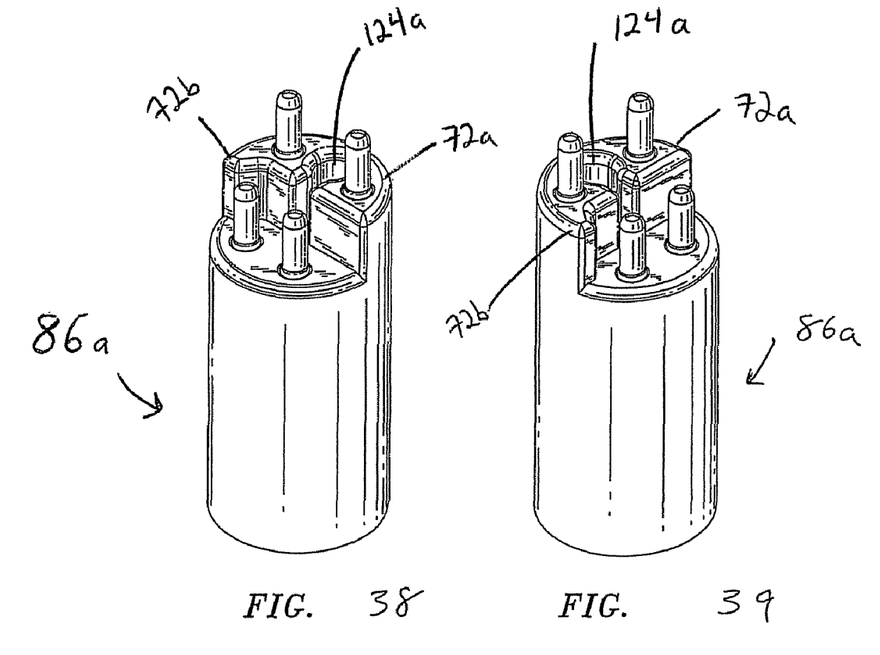
FIGS. 38-39 are perspective views of a lamp base useable with the socket of shown in FIGS. 30-37.
Figure 40:
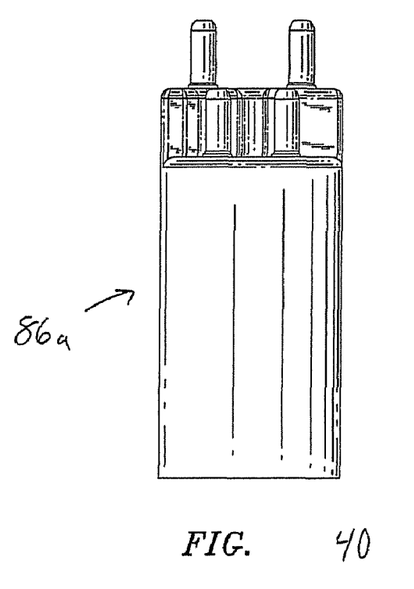
FIGS. 40-43 are side views of the base shown in FIGS. 38-39.
Figure 41:
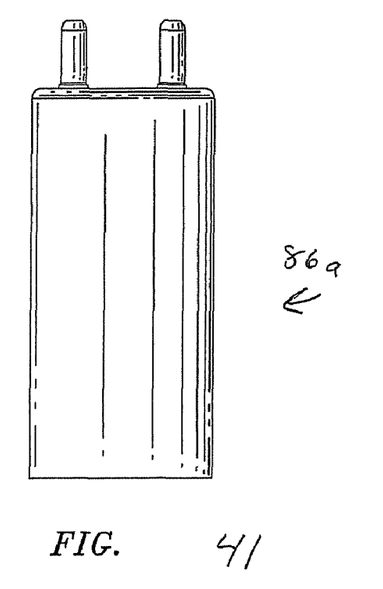
Figure 42:
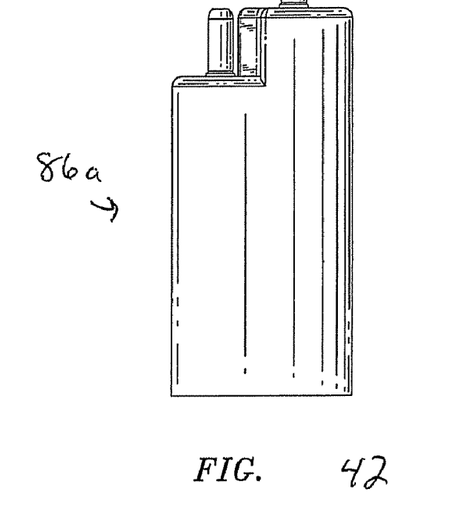
Figure 43:
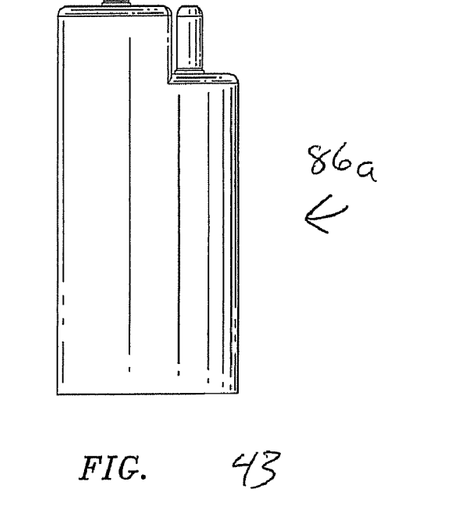
Figure 44:
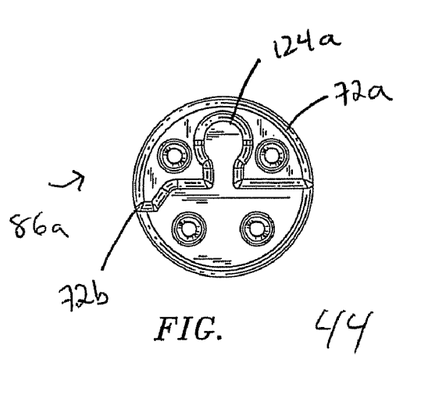
FIG. 44 is a top plan view of the base shown in FIGS. 38-43
Figure 45:
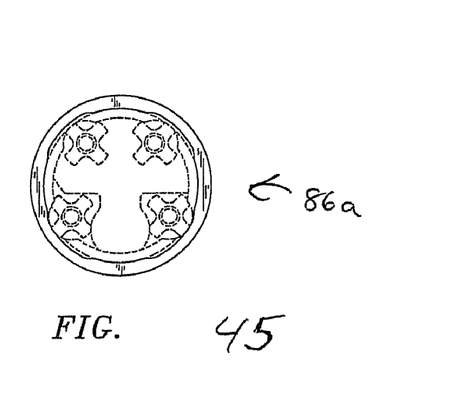
FIG. 45 is a bottom plan view of the base shown in FIGS. 38-44.

Similarly, with reference to FIGS. 25-29 and 30-37, receptacles or bases are shown which are configured to mate with the end caps of FIGS. 20-24 and 38-45, respectively. Thus, receptacle 30' of FIG. 25 includes male extension 132 which is sized and configured to be received by recess 122 in FIG. 20. Receptacle 30a of FIGS. 30-37 includes male extension 134a which is sized and configured to be received by recess 124a in FIG. 38. FIG. 38 also shows how semi-circular bases 72a may contain an asymmetrical section 72b which may be added to help ensure that unauthorized parts are unable to be used. This is a safety feature because improper wattage lamps or improper lamp designs may commonly be attempted to be substituted so the asymmetrical section 72b helps to prevent this unsafe occurrence. The sockets shown on FIGS. 30-37 may be used with the corresponding end caps or bases shown in FIGS. 38-45 or the designs may be exchanged with each other, i.e., the end cap may look like the receptacle or base or vice versa. Receptacle 94' of FIG. 26 includes arcuate shaped male extension 134 which is sized and configured to be received by arcuate recess 124 in FIG. 21. Similarly, receptacle 96' of FIG. 27 includes a rectangular extension 136 which is sized and configured to be received by rectangular recess 126 of FIG. 22, receptacle 98' of FIG. 28 includes a square shaped extension 138 which is sized and configured to be received by squared shaped recess 128 in FIG. 23 and receptacle 100' of FIG. 29 includes a triangular shaped extension 140 which is sized and configured to be received by rectangular shaped recess 130 in FIG. 24.

It will be appreciated that all of the embodiments of the present invention represent an advance over the stepped cap configuration of the aforementioned '527 patent in that the use of the extension (or alternatively the recess) positioned centrally along the barrier wall will provide improved interlocking between the lamp and the receptacle and will also ensure proper orientation of the respective pins within the recesses of the receptacle.

In operation, the cover 26 is removed, and a lamp 32 is inserted into the interior of the sleeve 14 via the aperture in the support wall 18. After insertion, the socket 30 is connected to the pins 48, 50, 52, 54. Then the cover 26 is installed on the housing 12. Electrical wires 66,68 extend exteriorly of the socket to a non-illustrated electrical power supply. A voltage difference across the wires 66,68 is applied to both electrodes 40, 42 causing an electrical discharge within the tube. This discharge causes ultraviolet radiation to be emitted. This radiation passes through the light-transmissive wall of the sleeve 14 to irradiate the water contained in the space 16.

The aforementioned barrier wall 70a, 70b prevents arcing interiorly of the end cap 44 by physically separating the electrical connections between the pins 48, 50 and the wire conductor, on the one hand, and the electrical connections between the pins 52, 54 and the electrode 40, on the other hand. The pairs of pins are thus effectively isolated.

It will be understood that each of the elements described above, or two or more together, also may find a useful application in other types of constructions differing from the types described above.

While the invention has been illustrated and described as embodied in an ultraviolet lamp for use in water or other liquid or air purifiers, it is not intended to be limited to the details shown, since various modifications and structural changes may be made without departing in any way from the spirit of the present invention. Thus, the lamp of this invention need not be limited to lamps that emit ultraviolet radiation, nor be limited to use in a water purifier.

While preferred embodiments have been shown and described, various modifications and substitutions may be made thereto without departing from the spirit and scope of the invention. Accordingly, it is to be understood that the present invention has been described way of illustrations and not limitation.

What is claimed is:

1. A lamp, comprising:
    an elongated, hollow, arc tube extending along a longitudinal axis between opposite end regions and containing a gas;
    a pair of electrodes spaced apart along the longitudinal axis and respectively mounted within the arc tube at the end regions thereof;
    a first end cap and a second end cap respectively mounted at the end regions of the arc tube;
    a first pair of electrical pins electrically connected to one of the electrodes;
    a second pair of electrical pins electrically connected to the other of the electrodes; and
    wherein the pins are mounted on the first end cap, and are offset relative to each other along the longitudinal axis;
    the first end cap comprises a mutually parallel distal semi-circular base and a proximal semi-circular base, and a barrier wall extending between the distal and proximal bases;
    the barrier wall comprises either an extension extending outwardly therefrom along the proximal base or a recess extending inwardly therefrom along the distal base;
    the extension has a height that is equal to the distance between the distal base and the proximal base or the recess has a depth that is equal to the distance between the distal base and the proximal base; and
    the first pair of pins extend through the distal base and the second pair of pins extend through the proximal base.

2. The lamp of claim 1, wherein the distal base comprises an asymmetrical section or asymmetrical recess and the proximal base comprises a corresponding asymmetrical section or asymmetrical recess.

3. An end cap for a lamp, comprising:
    a tubular housing having pins mounted on an end thereof;
    wherein the pins are offset relative to each other along the longitudinal axis of the housing;
    the end comprises a mutually parallel distal semi-circular base and a proximal semi-circular base, and a barrier wall extending between the distal and proximal bases;

the barrier wall comprises either an extension extending outwardly therefrom along the proximal base or a recess extending inwardly therefrom along the distal base;

the extension has a height which is equal to the distance between the distal base and the proximal base or the recess has a depth that is equal to the distance between the distal base and the proximal base; and the first pair of pins extend through the distal base and the second pair of pins extend through the proximal base.

4. The end cap of claim 3, wherein the distal base comprises an asymmetrical section or asymmetrical recess and the proximal base comprises a corresponding asymmetrical section or asymmetrical recess.

* * * * *